United States Patent [19]

Calhoun

[11] 4,121,103
[45] Oct. 17, 1978

[54] CAUSTIC DETECTION SYSTEM

[75] Inventor: Fredrick L. Calhoun, Rolling Hills, Calif.

[73] Assignee: Industrial Dynamics Company, Ltd., Torrance, Calif.

[21] Appl. No.: 739,059

[22] Filed: Nov. 5, 1976

[51] Int. Cl.² .................. G01N 21/24; G01N 21/34
[52] U.S. Cl. ............................. 250/343; 250/339; 250/564; 250/573; 250/576
[58] Field of Search ............. 250/339, 343, 344, 345, 250/346, 564, 573, 576

[56] References Cited

U.S. PATENT DOCUMENTS

| 3,652,850 | 3/1972 | Briggs | 250/573 X |
| 3,784,307 | 1/1974 | Jackson et al. | 250/339 X |
| 4,006,358 | 2/1977 | Howarth | 250/339 |
| 4,011,451 | 3/1977 | Nelson | 250/343 |

Primary Examiner—Archie R. Borchelt
Attorney, Agent, or Firm—Ellsworth R. Roston

[57] ABSTRACT

An inspection system for detecting the presence of an aqueous base solution in the bottom of a container including means disposed relative to the container for directing energy including at least energy in the infrared region through the bottom of the container and along the central axis of the container, and means disposed relative to the container for detecting the energy of particular infrared wavelengths passing from the bottom of the container and for producing signals in accordance with such detection and with the presence of an aqueous base solution providing for the absorption of the energy at the particular infrared wavelengths and with the absence of an aqueous base solution allowing for the passage of the energy at the particular infrared wavelengths.

30 Claims, 14 Drawing Figures

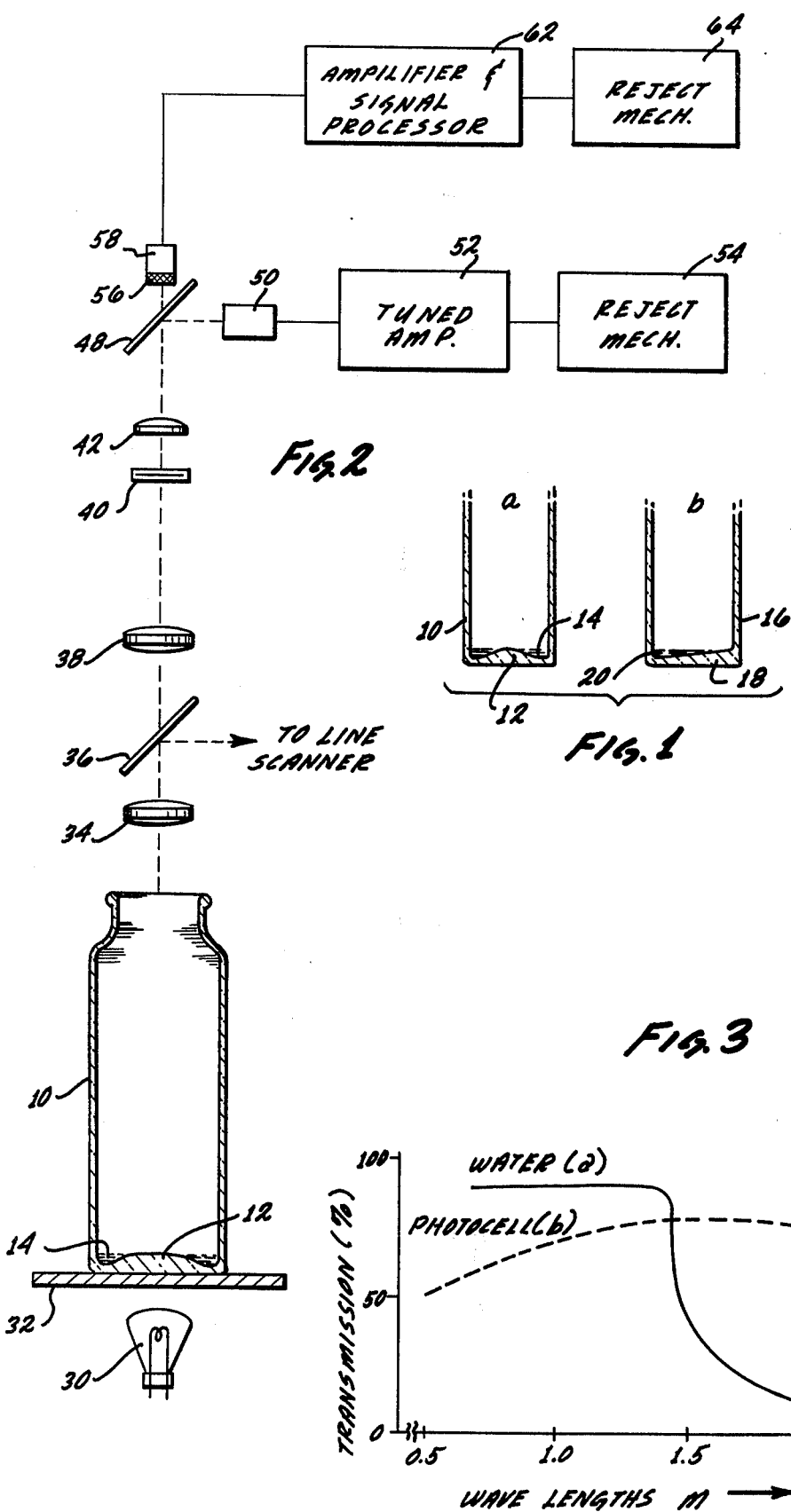

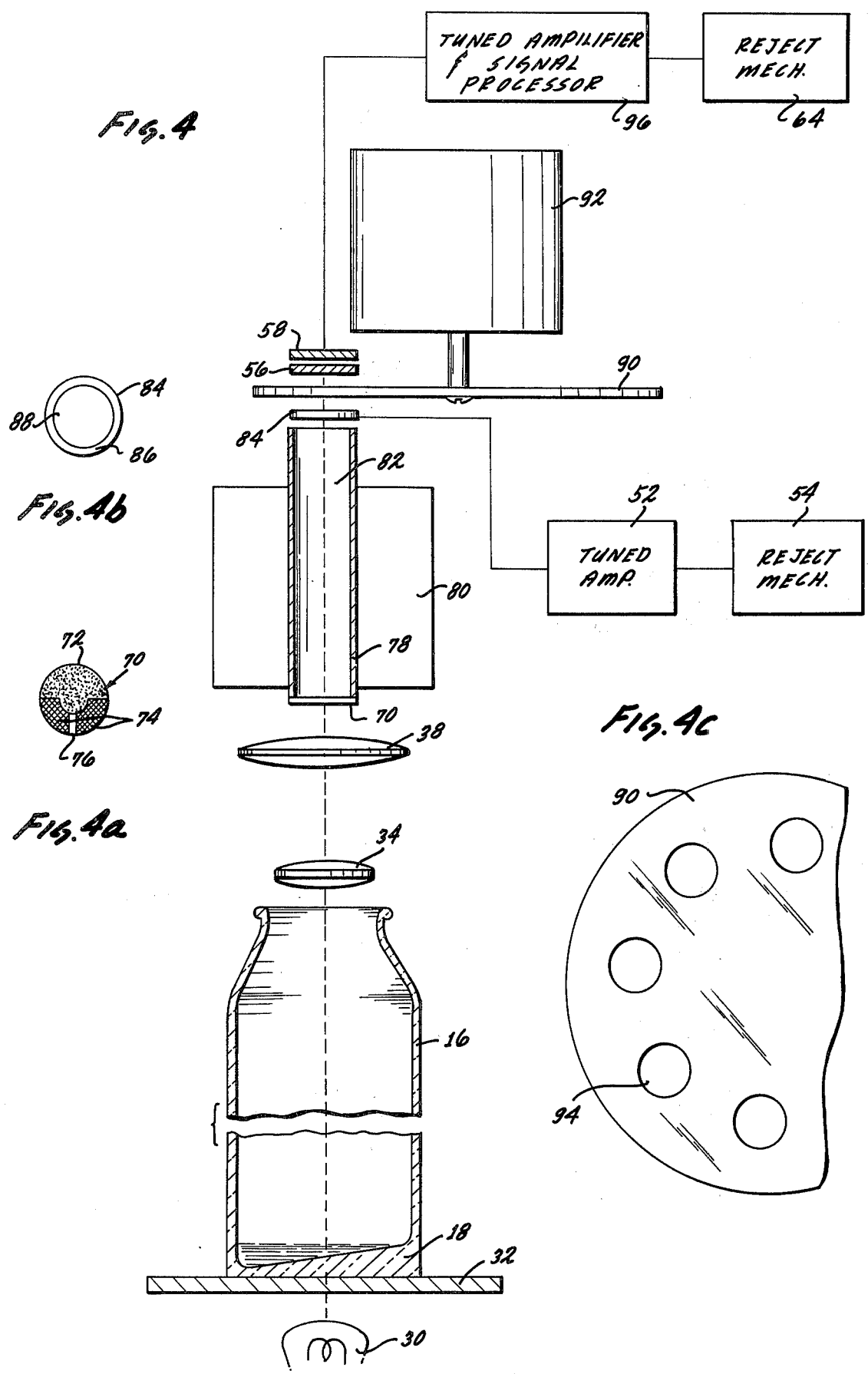

CAUSTIC DETECTION SYSTEM

The present invention is directed to an infrared system for detecting the presence of caustic solutions in a container such as empty soft drink or beer bottles. Specifically, during the reprocessing of returnable bottles, the bottles are cleaned of any residue using a caustic solution which is generally an aqueous solution of a caustic dissolved in water. The caustic solution is then rinsed out of the bottle to present a clean, empty bottle for refilling. It is possible, however, that during the rinse cycle some small residue of the caustic solution may be remaining at the bottom of the bottle. This is certainly undesirable from the consumer standpoint and those bottles should be removed from the production line.

The infrared detection of the aqueous base caustic solution may also be provided in combination with inspection of the bottle for other identifying characteristics such as contaminants, i.e., foreign particles, in the bottle. In particular, the present invention also provides for a unique method of incorporating such an infrared detection of caustic solution as part of an existing empty bottle scanning system.

The caustic solution which is to be detected consists of an aqueous solution of a caustic such as lye dissolved in water. It is known in the prior art that water acts as a filter passing radiation in the visible spectrum while absorbing radiation in certain portions of the infrared spectrum. It should be noted that in this disclosure the term "visible" when relating to photocells, filters, etc., includes the wavelengths where most common photoresistive and photovoltaic devices respond. This usually extends out past 1 micron in wavelength which is past the human eye visual response. The term "visible" herein is used to denote it from the infrared wavelengths where water absorption starts taking place. In other words, if water is present in the bottom of a container, such as a bottle, particular wavelengths of infrared radiation will be absorbed by such water while other visible wavelengths will pass through the water.

As an example, the use of infrared detection has previously been incorporated in a system for detecting the level of aqueous base-fluids in a container and such a system is disclosed in my prior U.S. Pat. No. 3,225,191 issued Dec. 21, 1965. In this prior patent, radiant energy is directed through the side of a container to detect a level of liquid in the container in accordance with the previously described infrared detection principle. Such a system, while suitable for the detection of a relatively high level of liquid, normally in the upper portion of the container, is not suitable for the detection of a caustic solution since the level of a caustic solution, if present in the bottle bottom, is normally very low and is often hidden by the variations of glass thickness in the bottom of the bottle. Therefore, it would not be possible to accurately detect the level of the caustic solution using energy directed through the side of the bottle, other than a gross detection of a relatively high level.

The present invention provides for the detection of a very low level of caustic solution in the bottom of the bottle and with the energy source directed through the bottle along an axis passing through the center of the bottle. Preferably, the energy source is directed upward through the bottom of the bottle to the detection system positioned above the neck opening. The detection system would normally include an optical system for directing the energy from the field of view of the bottom of the bottle to a photocell responsive to the proper infrared wavelengths. An infrared filter would normally be included to pass only wavelengths of infrared energy to the photocell that are absorbed by the aqueous base caustic solution.

In one specific embodiment of the invention, the infrared caustic detection system is incorporated as part of an empty bottle inspector for detecting the presence of foreign particles at the bottom of the bottle. In this particular system, radiant energy containing both visible and infrared wavelengths is transmitted through the bottle bottom, with a portion of the energy directed to a photocell responsive to wavelengths in the visible region and with another portion of the energy directed to a photocell responsive to wavelengths in the infrared region. As an example, a beam splitting mirror may be used to direct the radiant energy to the two photocells. The bottle bottom may be scanned in the visible region using a rotating reticle opaque to visible wavelengths to provide for the detection of foreign particles and with the same reticle providing for a substantial passage of energy in the infrared region for the detection of a caustic solution.

In another embodiment of the invention, the infrared detection of a caustic solution is accomplished in combination with an empty bottle inspector wherein the particle detection photocell, responsive to energy in the visible region, is designed to pass a portion of the infrared radiation so that the detection of both the energy in the visible spectrum and in the infrared spectrum is along a common optical axis. Other aspects of the invention include the use of an energy chopper to provide for an alternating output signal to the infrared photocell so it may operate at relatively low radiation levels with a minimum of drift in the associated electronic circuitry. Other aspects of the invention include a particular rotating reticle system for use in scanning the image of the bottom of the bottle for the detection of foreign particles in the visible region while, at the same time, providing for the scanning of the bottle bottom for minute traces of caustic solution using infrared energy.

A clearer understanding of the invention will be had with reference to the following description and drawings wherein FIGS. 1a and 1b illustrate a series of bottles having different bottom configurations and showing in each a small amount of a caustic solution remaining in the bottle after cleaning;

FIG. 2 illustrates in general form an embodiment of the invention for detecting the caustic solution using an infrared scanning detector as part of an empty bottle inspector;

FIG. 3 illustrates a series of graphs showing transmission characteristics relative to wavelength for various portions of the system of the present invention;

FIG. 4 shows a specific embodiment of the invention for providing the detection of caustic solution with an infrared detector and particle detection with a separate visible detector, both on a common axis;

FIG. 4a illustrates a particular reticle design for use with the embodiment of FIG. 4;

FIG. 4b illustrates a particular photocell design for use with the embodiment of FIG. 4;

FIG. 4c illustrates a particular mechanical energy chopper design for use with the embodiment of FIG. 4;

Figure 1C:
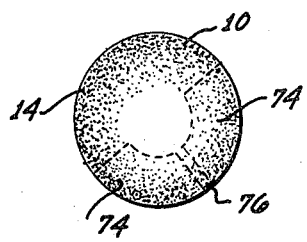
FIG. 1c illustrates the bottom of the bottle shown in FIG. 1a with the reticle pattern shown in FIG. 4a superimposed in dotted lines.

FIGS. 1a, 1b, 1c and 1d illustrate two different types of bottles, each having a different bottom configuration. Specifically, in FIGS. 1a and 1c, a bottle 10 has a thickened portion 12 in the center of the bottom of the bottle. This is normally the configuration for a very high percentage of bottles which are produced and are marketed. Essentially, the bottom of the bottle has a circular hump 12 so that a small amount of caustic solution designated by reference numeral 14 in the bottom of the bottle would have a doughnut shaped configuration as shown in FIG. 1c. It is desirable to detect the small amount of caustic solution as shown in FIG. 1a and even smaller amounts, but if light energy were directed through the side of the bottle 10, it would not be possible to detect the level of caustic solution as shown in FIG. 1a because the detection would be masked by the hump 12.

Figure 1D:
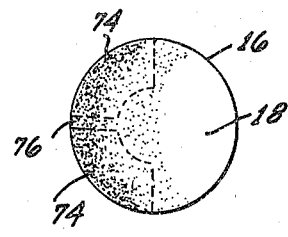
FIG. 1d illustrates the bottom of the bottle shown in FIG. 1b with the reticle shown in FIG. 4a superimposed in dotted lines.

FIGS. 1b and 1d illustrate a second configuration for a bottle 16 having a sloping bottom portion 18. This type of bottle configuration is present in a relatively small number of bottles produced and marketed. It is desirable to detect at least a level of caustic solution 20 designated by reference numeral 20, but, again, it can be seen that the thickest part of the sloping bottom 18 would prevent the detection of the caustic solution if the light energy were directed to the bottle 16 from a side position.

The present invention is directed to a system for providing for the detection of the caustic solution, such as shown by caustic solution 14 and 20 in FIGS. 1a and 1b. The detection is provided for levels of caustic solution as shown in FIGS. 1a and 1b, and even for lower levels of such caustic solution. Specifically, the detection of such small quantities of caustic solution in the bottom of the bottle may be accomplished using an infrared detection system as shown in FIG. 2.

In FIG. 2, the detection of caustic solution in the bottom of the bottle is shown for the type of bottle illustrated in FIG. 1a which is, as indicated above, the type of bottle normally produced and supplied to a consumer. The overwhelming percentage of bottles are of the type of bottle 10 shown in FIG. 2. As indicated above, this bottle has a hump 12, or raised portion, in the center of the bottom of the bottle. Caustic solution as designated by reference numeral 14 would normally collect around this hump and may actually represent a level of caustic solution even less than that shown in FIG. 2.

A radiant energy source 30 directs energy through a diffuser 32 through the bottom of the bottle and to a primary objective lens 34. It is to be appreciated that the bottle 10 would be one of a large number of bottles traveling on a conveyor line and which are positioned for inspection a relatively short period of time. Normally, these bottles are already being inspected after cleaning for the presence of foreign particles through the use of empty bottle inspectors which normally include the light source 30, lens 32, and primary objective lens 34. In addition, other portions of the system of FIG. 2, as will be explained, also are normally part of the empty bottle inspector system of the prior art. The present invention may be uniquely incorporated in such a system so that the inspection for caustic occurs at the same time as the inspection for foreign particles and uses a portion of the optical system for foreign particle inspection. The light source 30 provides for an output of radiant energy in both the visible region and in the infrared region of the spectrum.

The energy passing through the primary objective lens 34 may be directed to a beam splitting mirror 36. The beam splitting mirror may be incorporated in the particle detection system if the scanning for the detection of foreign particles or for other types of pattern recognition includes a transverse or line scanner in addition to the normal radial reticle scan provided by the prior art inspectors. In such a case, a portion of the energy is reflected by the beam splitter 36 to a line scanner as indicated in FIG. 2. The other portion of the energy is passed by the beam splitter 36 to a secondary objective lens 38. If the inspection system includes the additional transverse scan, such a system may be of the type described and claimed in co-pending application, Ser. No. 738,679, filed Nov. 4, 1976 in the name of Fredrick L. Calhoun and James Paul Douglass and assigned to the same assignee as in this application.

The image of the bottom of the bottle will normally be focused by lenses 34 and 38 on a rotating reticle 40. This reticle may be of the type provided in the prior art which includes alternating transparent and opaque areas and may actually have a single transparent and a single opaque area with either one or the other of the areas being a single spoke. The rotating reticle 40 will therefore provide for an alternating output signal if any foreign objects are in the field of inspection. The presence of the caustic solution 14 has essentially no effect on the level of visible energy passed through the optical system from the bottle 10 in the region of wavelengths where the particle detection system is operating. The energy passing from the reticle 40 impinges on a condensing lens 42.

The light energy passing from the condensing lens 42, therefore, still includes the complete spectrum of radiant energy in both the visible and infrared regions. The energy is then directed to a beam splitting mirror 48 which passes a portion of the energy and reflects another portion of the energy. For example, a portion of the energy may be reflected to a photocell 50 for the detection of energy in the visible region. The detection of the energy by the photocell 50 may represent the presence of any foreign particles in the bottom of the bottle. The detection would be on the basis of a particular alternating signal being generated if a foreign particle was on the bottle bottom. The output of photocell 50 is applied to a tuned amplifier 52 which passes and amplifies frequencies representative of the foreign particles, but discriminates against noise and other extraneous signals. The output signal from the tuned amplifier is applied to the reject mechanism 54 which is used to control the acceptance or rejection of the bottle 10 in accordance with the detection of foreign particles in bottle 10.

The other portion of the radiant energy which is passed by the beam splitter 48 is coupled to an infrared filter 56. This device operates as a low-pass optical filter to pass only energy at the longer wavelengths representative of the infrared region and to discriminate against energy at the shorter wavelengths representative of the visible region. It is to be appreciated that the beam splitting mirror 48 may in itself incorporate an infrared filter so that energy in the visible spectrum would be reflected to the photocell 50 while energy in the infrared region would pass through the mirror 48 for coupling to the infrared detection portion of the system.

The energy in the infrared region is then coupled to an infrared photocell 58 which detects the presence or absence of energy in the infrared region. The output from the infrared photocell 58 is passed to the amplifier and signal processing circuits 62. The signals from these circuits are used as an input to a reject mechanism 64 for the rejection of the bottle 10 upon the presence of caustic solution in the bottom of the bottle.

FIG. 3 illustrates various transmission characteristics of portions of the system of FIG. 2 and the operation of the system will best be understood with reference to FIG. 3. In FIG. 3, curve (a) shows the energy transmission characteristics for water. It is to be appreciated that the caustic solution is an aqueous solution composed of a small amount of caustic dissolved in water.

It can be seen that the transmission characteristics for water generally include a relatively high transmission for energy of short wavelengths through the visible region and with a rapid absorption of the energy by water for wavelengths longer than 1.5 microns. It can be seen, therefore, that if water in the form of a caustic solution is present in the bottom of the bottle 10, then even very minute thickness of such water will provide for an appreciable absorption of the energy in the far infrared region. If no caustic solution or a negligible amount of caustic solution is present at the bottom of the bottle 10, then essentially all of the energy in both the visible and infrared regions would be passed by the glass bottle bottom to both photocells.

As shown in FIG. 3, the glass provides for a cutoff of the transmission of all energy having wavelengths longer than 2.5 microns. In order to ensure that the energy passed to the photocell 58 is only infrared energy longer than 1.5 microns the infrared filter 56 and/or the use of a beam splitting mirror which includes an infrared filter is designed to have a filter characteristic as shown by curve (c). It can be seen that this filter characteristic has a very sharp cutoff for wavelengths shorter than 2 microns so that even though the photocell 58 may be responsive to energy over a broad spectrum as shown by the curve (d) in FIG. 3, only wavelengths longer than 2 microns are passed to the photocell 58. Therefore, the detection of infrared energy by the photocell 58 represents the absence of any caustic solution in the bottom of the bottle since no water is present to absorb this infrared energy. However, the presence of even a minute thickness of water provides for an appreciable absorption of the infrared energy and thus the energy in the infrared region received by the photocell 58 is reduced. Therefore, a null in the output signal represents the presence of a caustic solution in the bottom of the bottle 10. The amplifier and signal processing circuits 62 therefore provide for an output signal representative of the presence of the caustic solution in the bottle 10 so that the reject mechanism 64 provides for the acceptance or rejection of the bottle 10 in accordance with the absence or presence of caustic solution in the bottle.

The sensitivity of the caustic solution detection system can be greatly enhanced by utilizing the scanning capabilities of the particle detection reticle. This explanation of such a system will be described in the explanation of FIG. 4.

The photocell 50 may be any type of a photocell which is responsive to energy in the visible region. For example, a solar cell, photovoltaic type of photocell, provides for the proper response to the detection of the energy representative of foreign particles. The photocell 58 must be responsive to energy in the infrared region and also must have a good frequency response characteristic, since the cell is illuminated when no caustic solution is present and the illumination is reduced when caustic solution is in the bottle 10. One type of cell which is suitable for this type of detection is a lead sulphide photocell which is a photoresistive element to provide for a change in resistance of the element in accordance with the illumination by infrared energy. This type of photocell has a frequency response characteristic ranging from DC to very high frequencies. Its temperature stability characteristics, however, are rather unstable in the DC mode of operation. This photocell operates best when it can be AC coupled to the electronic circuitry.

FIG. 4 illustrates another embodiment of the invention showing the use of infrared detection for a caustic solution as part of an empty bottle inspector and including several additional features. In FIG. 4, the bottle is shown to be of the type illustrated in FIG. 1b having a sloping bottom 18 in the bottle 16. It is to be appreciated, however, that either of the types of bottles shown in FIGS. 1a and 1b would operate properly and even bottles with different configurations at the bottom would have the presence of the caustic solution detected by the present invention. As long as a relatively minute thickness of caustic solution is present at the bottom of the bottle, the present invention will provide for the detection of such caustic solution.

The light source 30 which provides for radiant energy in both the visible and infrared region, directs this energy through the diffuser 32 and through the bottom of the bottle to the primary objective lens 34 which is part of the focusing system for focusing the energy for detection. The energy from the primary objective lens is additionally focused by the secondary objective lens 38. It is to be appreciated that although the system of FIG. 4 does not include a beam splitter 36 as shown in FIG. 2, such a beam splitter may be used to direct energy to a transverse or line scanner for further detection of characteristics such as foreign particles in the manner described in the co-pending application referred to above.

The energy from the bottle bottom is focused by the lenses 34 and 38 and imaged on a rotating reticle 70 which may have the unique design as shown by the detail of the reticle in FIG. 4a. The reticle 70 includes a portion 72 which is opaque to both visible and infrared radiation and may be, for example, a metal mask. The crosshatched portion 74, which includes two segments, is a filter which is opaque to the visible region of the spectrum but transparent to infrared energy. Finally, a clear slit 76 is transparent to radiation in both the visible and infrared regions. It can be seen, therefore, that as the reticle 70 rotates, the reticle provides for a single spoke 76 for scanning the visible region of the spectrum for the detection of characteristics such as foreign particles. In addition, the portions 74 and the slit 76 operate to pass a large segment of the infrared radiation, and provide for selective scanning of the infrared radiation from the bottle bottom to improve the resolution of the system.

The center portion of the reticle is masked since it is not a significant factor in the detection of foreign particles using the visible radiation but this design results in increased sensitivity for the caustic solution scanning system. This can be explained by FIGS. 1a, 1b, 1c, 1d, and 4a. FIGS. 1c and 1d are top views of the bottoms of the bottles 10 and 16 shown in FIGS. 1a and 1b. The shaded portion is the caustic solution as seen by the infrared photocell and filter combination. It will be noticed that the darkened area of FIG. 1c is shaped like a doughnut, with the middle hole transmitting more infrared energy, since there is little or no solution in the middle due to the hump in the bottom. FIG. 1d has half the bottom shaded with increasing infrared attenuation at the edge where the caustic solution is the thickest. Both FIGS. 1c and 1d have the reticle pattern of FIG. 4a superimposed over them in dotted lines showing the infrared transparent portions 74. In FIG. 1c, which is by far the most predominant type of bottle on the production line, the center portion that has very little infrared attenuation is masked by the opaque center portion of the reticle. All the infrared radiation, therefore, must pass through the sections 74 and 76 where the maximum attenuation occurs due to the caustic solution. In this particular case, regardless of how the reticle is rotated essentially a constant attenuation is encountered due to the doughnut shaped caustic solution field as shown in the graph in FIG. 5. So in the case of the bottle of FIG. 1c, blocking the center of the field helps increase the sensitivity to the caustic solution since the major area where there is no caustic solution is masked.

In FIG. 1d, the reticle pattern is positioned in rotation so the infrared transparent portions 74 and 76 are over the area where there is maximum attenuation of the infrared energy by the caustic solution. This corresponds to the 0° and 360° positions in FIG. 5. As the reticle rotates the relative output from the photocell increases to a maximum at 180°, where there is very little caustic solution present to block the infrared radiation. During the signal processing by processor 96, the null portion of the photocell output is chosen, as the reticle rotates, to obtain the optimum caustic solution detection capability. The use of a reticle for scanning the bottle bottom exceeds the capabilities of a system that looks at the entire bottle bottom at one time because the maximum point of caustic solution attenuation may be used. Scanning with a particular shaped reticle design will also greatly increase the sensitivity of the caustic detection system to small non-uniformly patches of solution on the bottom of the bottles.

Figure 4D:
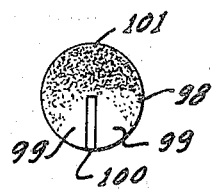
FIG. 4d illustrates another reticle design utilizing a narrow spoke that is opaque to visible energy and a gradiant around the remaining portion of the reticle that is opaque to infrared energy.
Figure 5:
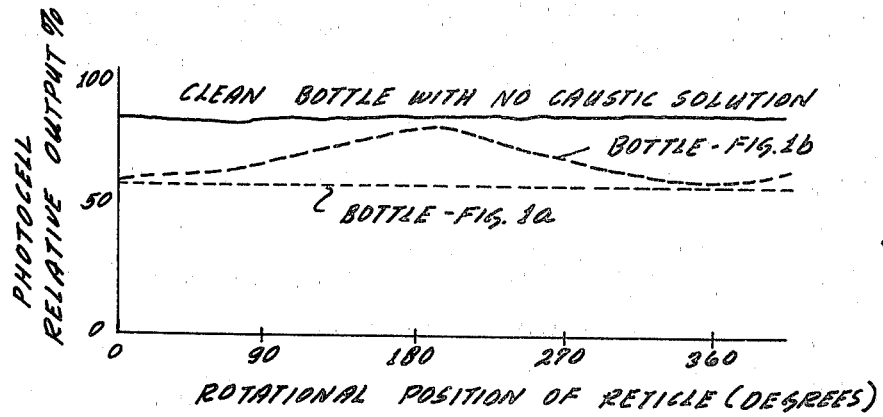
FIG. 5 illustrates a graph that shows the infrared photocell output as a function of the rotational position of the reticle shown in FIG. 4a while scanning bottles shown in FIGS. 1a and 1b and a clean bottle with no caustic.

FIG. 4d shows another reticle design 98 that may be employed using an opaque spoke 100 for foreign particle detection. The areas 99 are transparent to both the visible and infrared radiation and slowly blend into a fully opaque mask in the area of 101. This allows only the spoke 100 to scan for foreign particles since the gradient areas do not yield good chopping efficiency on small objects. The area where the infrared radiation can pass will give the field scanning capabilities required for the caustic detection.

Figure 4E:
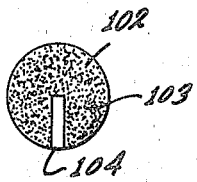
FIG. 4e illustrates a reticle that has a narrow spoke that is transparent to both visible and infrared energies and the remaining portion is opaque to invisible and infrared energy.

FIG. 4e is yet another design 102 where there is a single spoke 104 that is transparent to both visible and infrared radiation and all the remaining portion 102 is opaque to both. This design greatly reduces the instantaneous field of the infrared scan coverage which in certain cases can increase the sensitivity of that system, but also reduces significantly the infrared. It should be pointed out that many such reticle designs will work in the disclosed invention and those illustrated are merely illustrative of particular designs employed on particular bottle configurations.

It should also be understood that the small spokes 76 and 100 in the reticle designs of 4a and 4b could be eliminated and the system would perform satisfactorily in only the caustic detection mode. The small spoke allows the system to function in both modes at the same time but in some instances only a caustic or water detector is required. Under these conditions photocell 84 and the associated circuitry 52 and 54 would be eliminated but all other components would be retained.

The reticle 70 is mounted at the lower end of a rotor 78 which rotates as a hollow shaft within a motor 80. Mounted at the top end of the hollow motor shaft is the reticle 70 and directly above that is a fixed photocell 84. Therefore, the reticle scans essentially all of the energy passing to the detecting portion of the system. The photocell 84 has the unique construction as shown in the detail view in FIG. 4b.

The photocell 84 is essentially a normal solar or photovoltaic type cell, but with a particular modification. Normally, a solar type photocell has its nonsensitive surface formed entirely of metallic conductive material. In this case a portion of this conductive back is removed to form a doughnut shaped ring of conductive material 86. This exposes the photocell in the central region 88 so as to allow for the passage of infrared energy through the solar cell 84 for detection by the infrared photocell 58. This can be accomplished since the solar cells are constructed of silicon which is semitransparent to infrared energy. Specifically, the solar cell 84 operates in the normal manner to provide for the detection of energy in the visible region but in addition allows for the passage of infrared energy through the solar cell for detection by the infrared photocell 58. Solar cell 84 is essentially responsive to the energy in the visible spectrum but does not block the energy in the infrared spectrum. It is not necessary for the conducting portion to cover the entire back since it is only necessary to provide for a conducting segment 86 in communication with the back side of the solar cell. In fact, it would be possible to have even a small spot of conductive material in contact with the back side of the solar cell and the solar cell would still operate in the proper fashion. It is to be appreciated that the solar cell 84 may be constructed by removing a portion of the conductive back from a normal solar cell, such as by etching, or the solar cell 84 may be manufactured to have the configuration shown in FIG. 4b.

As indicated above, the infrared photocell 58 detects the presence or absence of caustic in the bottle because the caustic solution is essentially water and water operates to absorb energy in a particular infrared region. If caustic is present, energy in this particular infrared region is absorbed by the caustic solution and the radiation to the infrared photocell is reduced. If, on the other hand, no caustic solution is present then the infrared energy is increased to the infrared photocell 58. The infrared filter 56 helps to ensure that the infrared photocell 58 receives only energy in the infrared region beyond the cutoff of water as explained above with reference to FIG. 1 and FIG. 3.

The embodiment of FIG. 4 also includes a mechanical chopper in order to increase the stability of the electronic amplifying system since it can be AC coupled throughout. The chopper eliminates the DC drift problems associated with this type of infrared detector and greatly increases the overall sensitivity of the detection system. Specifically, the chopper system includes a chopper disc 90 rotated by a motor 92 to interrupt the infrared energy directed to the infrared filter 56 and the photocell 58.

Figure 5A:
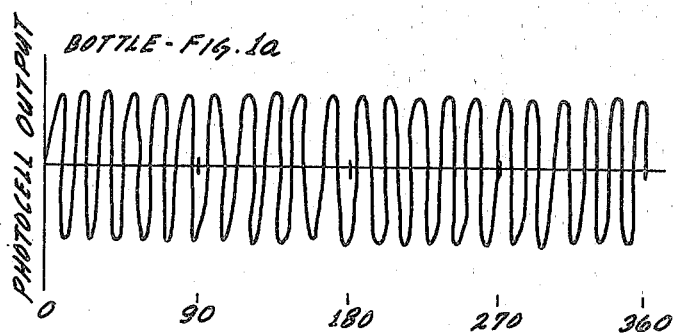
FIG. 5a illustrates the modulated signal received at the photocell from the bottle shown in FIG. 1a due to the energy chopper.
Figure 5B:
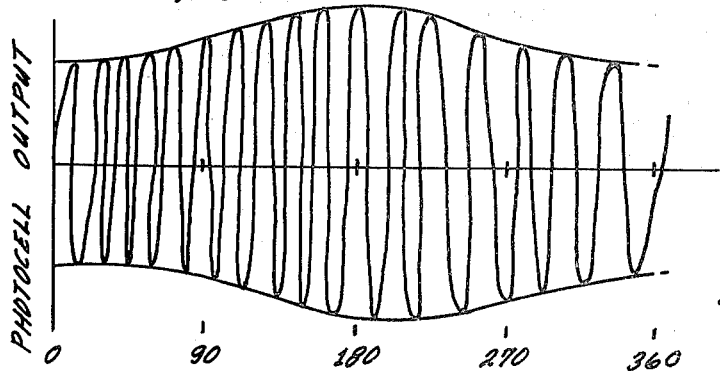
FIG. 5b illustrates the modulated energy received by the photocell from the bottle shown in FIG. 1b due to the energy chopper.

As shown in the detail of the chopper disc 90 in FIG. 4c, the chopper disc 90 is an opaque disc including a plurality of openings 94 which chop the infrared energy directed to the infrared photocell 58 in accordance with the speed of the motor 92 and the number of openings 94 around the disc 90. The tuned amplifier and signal processing system 96 is included in the electrical detection portion of the system and has a frequency response in accordance with the frequency of the chopper energy detected by the infrared photocell 58. As discussed before, the energy chopper is used for the benefit of the infrared channel only due to the nature of the infrared detectors. The chopper or modulated waveforms as seen by the infrared photocell is shown in FIGS. 5a and 5b. FIG. 5a is the chopped output as shown in curve 1a in FIG. 5. The signal is a constant amplitude and frequency that has been attenuated by the caustic solution. FIG. 5b corresponds to curve 1b in FIG. 5 and shows the null in the modulation at 0° and 360° where the maximum attenuation due to the caustic solution occurs. The electronic circuits are designed to detect a null in the envelope during the scanning cycle. A null of sufficient magnitude signifies an amount of caustic solution that should be rejected.

It can be seen that the embodiment of FIG. 4 includes an infrared detection for the presence of caustic solution in a bottle and specifically provides for this detection in combination with an empty bottle inspector. Specifically, the embodiment of FIG. 5 includes unique features including a specifically designed rotating reticle having a particular configuration providing for the scanning of the visible energy region with a single spoke reticle for foreign particles and also allowing for the scanning of energy in the infrared region for caustic detection. In addition, a first photocell is a solar cell having a portion of the back conducting surface removed so that the photocell detects energy in the visible region while passing energy in the infrared region for detection by a second photocell.

It is obvious that the caustic scanning system could be operated alone without combining it with the empty bottle inspector for foreign particles, but there are advantages of combining the systems particularly with respect to the space considerations. The present invention, therefore, provides for the detection of caustic while reducing the overall cost of the system since it may be incorporated within an empty bottle inspector and uses a substantial portion of the optical and scanning system of the empty bottle inspector.

This principle of caustic detection can be used with other methods of empty bottle inspection systems such as rotating dove prism and spinning mirror scanners, and it not limited to the rotating reticle system.

Although the present invention has been described with reference to particular embodiments, it is to be appreciated that various adaptations and modifications may be made and the invention is only to be limited by the appended claims.

I claim:

1. An inspection system for detecting the presence of an aqueous base solution in the bottom of a container, including,
   means disposed relative to the container for directing energy including at least energy in the infrared region through the bottom of the container and along the central axis of the container, and
   means disposed relative to the container for detecting the energy of particular infrared wavelengths passing from the bottom of the container and for producing signals in accordance with such detection and with the presence of an aqueous base solution providing for the absorption of the energy at the particular infrared wavelengths and with the absence of an aqueous base solution allowing for the passage of the energy at the particular infrared wavelengths.

2. The inspection system of claim 1 wherein the means for detecting the energy at the particular infrared wavelengths includes a filter means for only passing the energy at the particular infrared wavelengths and a photocell for detecting the energy at the particular infrared wavelengths.

3. The inspection system of claim 2 wherein the filter means is a low-pass infrared filter that only passes infrared wavelengths that are longer than the cutoff characteristics of water.

4. The inspection system of claim 1 additionally including means for chopping the energy received by the means for detecting.

5. The inspection system of claim 1 wherein the energy also includes energy in the visible region and additionally includes means disposed relative to the container for detecting the energy in the visible region passing from the container for providing signals in accordance with such detection and with the presence of foreign particles in the container providing for a change in the characteristics of the energy in the visible region passing from the container.

6. The inspection system of claim 5 additionally including means for directing the energy in the visible region to the means for detecting such visible energy and for directing the energy in the infrared region to the means for detecting such infrared energy.

7. The inspection system of claim 5 wherein the means for detecting the energy in the visible region is transparent to the energy in the infrared region and with the means for detecting the energy in the infrared region disposed relative to the means for detecting the energy in the visible region for receiving the infrared energy passing through the means for detecting the visible energy.

8. The inspection system of claim 7 wherein the means for detecting the visible energy is a solar cell having a conductive back extending over a back portion of the solar cell and with the portion over which the conductive back extends not interferring with the passage of the infrared energy through the solar cell.

9. The inspection system of claim 5 additionally including a rotating reticle for interrupting the energy passing from the container and with the reticle including a first portion for passing the visible light energy and including a second portion for passing the infrared energy.

10. The inspection system of claim 9 wherein the first portion of the reticle is a spoke transparent to both the visible and the infrared energy and the second portion is at least a segment of the reticle larger than the spoke and overlapping the spoke for passing only the infrared energy.

11. An inspection system for detecting the presence of contaminants in the bottom of a container, including,
    means disposed relative to the container for directing energy including energy in the visible and in the infrared regions through the bottom of the container and along the central axis of the container,
    means disposed relative to the container for detecting the energy in the infrared region passing from the container and for producing signals in accordance with such detection and with the presence of a caustic solution providing for the absorption of the energy in the infrared region and with the absence of a caustic solution allowing for the passage of the energy in the infrared region, and
    means disposed relative to the container for detecting the energy in the visible region passing from the container for providing signals in accordance with such detection and with the presence of foreign particles in the container providing for a change in the characteristics of the energy in the visible region passing from the container.

12. The inspection system of claim 11 wherein the means for detecting the energy in the infrared region includes a filter for only passing the energy in the infrared region and a photocell for detecting the energy in the infrared region.

13. The inspection system of claim 11 additionally including means for chopping the infrared energy passing from the container and before the energy is detected by the means for detecting the infrared energy.

14. The inspection system of claim 11 additionally including beam splitting means for directing the portion of the energy in the visible region to the means for detecting such visible energy and for directing the portion of the energy in the infrared region to the means for detecting such infrared energy.

15. The inspection system of claim 11 wherein both detecting means are along a common optical axis and the means for detecting the energy in the visible region is transparent to the energy in the infrared region and with the means for detecting the energy in the infrared region receiving the infrared energy passing through the means for detecting the visible energy.

16. The inspection system of claim 15 wherein the means for detecting the visible energy is a solar cell having a conductive back extending over a circumferential portion of the solar cell not interferring with the passage of the infrared energy through the solar cell.

17. The inspection system of claim 11 additionally including a rotating reticle for interrupting the energy passing from the container, and with the reticle including first alternating opaque and transparent portions to the visible light energy and including second opaque and transparent portions to the infrared energy.

18. The inspection system of claim 17 wherein the first portions of the reticle includes a spoke transparent to both the visible and the infrared energy and wherein the second portions of the reticle includes a segment of the reticle larger than the spoke and overlapping the spoke for passing only the infrared energy.

19. In an inspection system for containers including a source of energy directed through the bottom of the container along a central axis of the container and including a means for scanning the energy passing from the container for modulating the energy in accordance with identifying characteristics and including a means for detecting such modulated energy, an improvement including,
    the source of energy additionally producing light energy in the infrared portion of the spectrum and with the infrared energy passing from the container in accordance with the absence of an aqueous solution in the bottom of the container and with the infrared energy absorbed in accordance with the presence of an aqueous solution in the bottom of the container,
    filter means responsive to the energy passing from the container for passing only the infrared energy, and
    detector means responsive to the infrared energy passing from the filter means for detecting the absence or presence of an aqueous solution in the bottom of the container in accordance with the presence or absence of infrared energy.

20. In the inspection system of claim 19 additionally including means for chopping the infrared energy passing from the container and before the energy is detected by the detector means.

21. In the inspection system of claim 19 additionally including beam splitting means for directing the portion of the energy in the visible region to the means for detecting such visible energy and for directing the portion of the energy in the infrared region to the means for detecting such infrared energy.

22. The inspection system of claim 19 wherein the detecting means is along a common optical axis with the means for detecting the modulated energy and the means for detecting the modulated energy is transparent to the energy in the infrared region and with the detecting means receiving the infrared energy passing through the means for detecting the modulated energy.

23. In the inspection system of claim 19 wherein the means for detecting the modulated energy is a solar cell having a conductive back extending over a circumferential portion of the solar cell and with such solar cell not interferring with the passage of the infrared energy through the solar cell to the detector means for the infrared energy.

24. In the inspection system of claim 19 wherein the scanner includes a rotating reticle for interrupting the energy passing from the container, and with the reticle including first alternating opaque and transparent portions to all of the energy and including second opaque and transparent portions to the infrared energy.

25. In the inspection system of claim 24 wherein the first portions of the reticle includes a spoke transparent to all of the energy and wherein the second portions of the reticle includes a segment of the reticle larger than the spoke and overlapping the spoke for passing only the infrared energy.

26. An inspection system for detecting the presence of an aqueous base caustic solution on the bottom of a container, including
    first means disposed relative to the container for directing radiant energy transverse to the bottom of the container through a path including the bottom of the container and the aqueous base caustic solution, second means disposed relative to the container for processing the portion of the radiant energy that passes through the bottom of the container and the aqueous base caustic solution, and third means operatively coupled to the second means for determining the presence of any caustic solution on the bottom of the container in accordance with the wavelength spectral characteristics of the processed radiant energy.

27. The inspection system set forth in claim 26, including, fourth means responsive to at least a portion of the radiant energy passing through the bottom of the container for determining the presence of foreign particles on the bottom of the container in accordance with the characteristics of the intercepted radiant energy.

28. The inspection system recited in claim 26, including, fourth means responsive to the radiant energy processed by the second means for determining the presence of foreign particles on the bottom of the container in accordance with the characteristics of such intercepted radiant energy.

29. An inspection system for detecting the presence of caustic in solution on the bottom of a container, including first means for directing radiant energy in a path transverse to the bottom of the container and including the bottom of the container and any solution on the bottom of the container, second means disposed relative to the container for intercepting the radiant energy passing through the bottom of the container and any solution on the bottom of the container and for selecting particular wavelengths of energy that are characteristic of the caustic in solution on the bottom of the container, and third means responsive to the radiant energy intercepted and selected by the second means for producing an output when there is caustic in solution on the bottom of the container.

30. The inspection system of claim 29 additionally including fourth means disposed relative to the container for intercepting at least a portion of the radiant energy passing through the bottom of the container for determining the presence of foreign particles on the bottom of the container in accordance with the characteristics of such intercepted portion of the radiant energy.

* * * * *